United States Patent [19]
Goettsch et al.

[11] 4,140,685
[45] Feb. 20, 1979

[54] PROCESS FOR RECOVERING ε-CAPROLACTAM FROM AN ε-CAPROLACTAM/SULFURIC ACID REACTION MIXTURE

[75] Inventors: Reijer Goettsch, Beek(L); Rudolf L. Zwart, Munstergeleen, both of Netherlands

[73] Assignee: Stamicarbon, B.V., Geleen, Netherlands

[21] Appl. No.: 810,568

[22] Filed: Jun. 27, 1977

[30] Foreign Application Priority Data

Jun. 28, 1976 [NL] Netherlands .................... 7607047

[51] Int. Cl.² .......................................... C07D 201/16
[52] U.S. Cl. ............................................. 260/239.3 A
[58] Field of Search ................................. 260/239.3 A

[56] References Cited
U.S. PATENT DOCUMENTS

| 3,852,272 | 12/1974 | DeRooij | 260/239.3 A |
| 3,852,273 | 12/1974 | DeRooij | 260/239.3 A |
| 3,859,278 | 1/1975 | DeRooij et al. | 260/239.3 A |
| 3,879,380 | 4/1975 | DeRooij et al. | 260/239.3 A |

Primary Examiner—Henry R. Jiles
Assistant Examiner—Robert T. Bond
Attorney, Agent, or Firm—Cushman, Darby & Cushman

[57] ABSTRACT

The process is directed to recovering ε-caprolactam from a reaction mixture containing ε-caprolactum and sulfuric acid by separating the caprolactam from the sulfuric acid by an extraction. Extraction includes the steps of neutralizing a part of said sulfuric acid with ammonia, ammonium sulfate, ammonium hydrogen sulfate or mixture thereof, to form an ammonium salt of at least part of said sulfuric acid as a neutralization product, thermally decomposing a part of the ammonium salt formed to produce a gaseous mixture of ammonia and sulfur dioxide and contacting another portion of the neutralization product with said gaseous mixture to produce ammonium hydrogen sulfate, ammonium sulfate or both, and neutralizing at least a part of the sulfuric acid in the reaction mixture with said ammonium hydrogen sulfate, ammonium sulfate or both.

1 Claim, 1 Drawing Figure

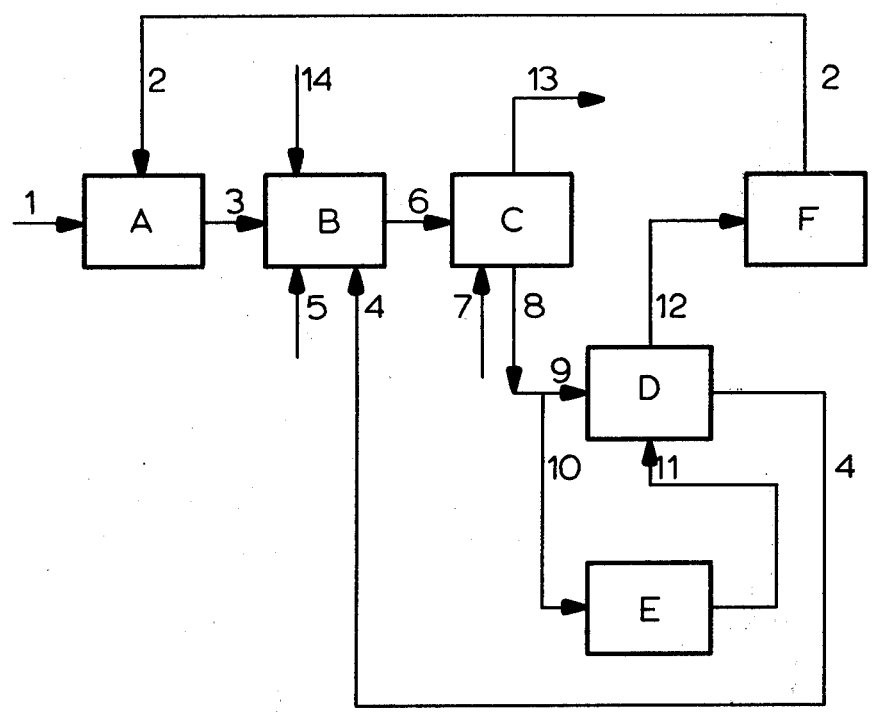

PROCESS FOR RECOVERING ε-CAPROLACTAM FROM AN ε-CAPROLACTAM/SULFURIC ACID REACTION MIXTURE

BACKGROUND OF THE INVENTION

The invention is directed to a process of recovering ε-caprolactam from reaction mixtures containing ε-caprolactam and sulfuric acid. Typically, these reaction mixtures may result from two different methods of producing ε-caprolactam, which is used to produce nylon-6. One of the synthetic routes for producing ε-caprolactam involves subjecting cyclohexanone oxime to a Beckmann rearrangement reaction by treating that oxime with sulfuric acid, oleum or sulfur trioxide. Another route involves reacting cyclohexane carboxylic acid with a nitrosating agent in the presence of sulfuric acid.

Because of the importance of ε-caprolactam, the art has developed various methods for recovering ε-caprolactam from sulfuric acid containing reaction mixtures. In all these methods, disadvantages inhere. For instance, U.S. Pat. No. 2,993,889 is directed to removing sulfuric acid from ε-caprolactam containing mixtures by neutralizing the sulfuric acid with ammonia water. The disadvantage of this process is that large unwieldy amounts of ammonium sulfate are produced as by-product which cannot serve a useful purpose. U.S. Pat. No. 3,336,298 attempts to overcome that drawback of U.S. Pat. No. 2,993,889 by converting the sulfuric acid of the ε-caprolactum containing reaction mixture into ammonium hydrogen sulfate rather than ammonium sulfate; concentrated solutions of ammonium hydrogen sulfate can be used in the dissolution of rock phosphate. In order to convert the sulfuric acid into ammonium hydrogen sulfate, the later patent teaches reacting the sulfuric acid with ammonium sulfate. This process obviates formation of ammonium sulfate by-product, but the efficiency of recovery of ε-caprolactam is then dependent on the production of an other product.

U.S. Pat. No. 3,852,272 obviates the result of formation of useless by-products by partly neutralizing the sulfuric acid in said mixtures with ammonia water, extracting the lactam from the partly neutralized mixture; and burning the ammonium hydrogen sulfate produced in said partial neutralization to produce sulfur dioxide which can be converted into sulfuric acid. The disadvantage of this method resides in the loss of the ammonia since during burning it is reduced to nitrogen and water. U.S. Pat. No. 3,879,380 obviates the formation of unuseful by-products and the combustion of ammonia, by partially neutralizing the sulfuric acid in ε-caprolactam containing mixtures to form a melt containing ammonium hydrogen sulfate and treating said melt with a suitable metal oxide, e.g. zinc oxide to recover ammonia and sulfur trioxide. This method or recovering ammonia and sulfur trioxide is extremely expensive.

DESCRIPTION OF THE INVENTION

The invention provides a simple process for the recovery of ε-caprolactam from a reaction mixture, which contains sulfuric acid. The process is not dependent economically on the production of by-products, and the combusion and loss of ammonia are substantially avoided.

The process, according to the invention, for recovering ε-caprolactum from a reaction mixture containing sulfuric acid, at least a part of the sulfuric acid being in the form of an ammonium salt thereof, by extracting said ε-caprolactam from said sulfuric acid, includes the additional steps of thermally decomposing a part of said sulfuric acid containing said salt to form a gaseous mixture of ammonia and sulfur dioxide; contacting an additional amount of said sulfuric acid containing said salt with said gaseous mixture wherein said ammonia reacts with sulfuric acid to form ammonium hydrogen sulfate, ammonium sulfate or both, and sulfur dioxide is discharged from said sulfuric acid as a gas; and using said ammonium hydrogen sulfate, ammonium sulfate or both to treat a mixture of ε-caprolactam and sulfuric acid with formation of additional amounts of said starting reaction mixture being subjected to the said extraction.

The step of thermally decomposing said sulfuric acid, at least part of which is in the form of an ammonium salt, into ammonia and sulfur dioxide can be accomplished by various methods. For instance, the ammonium salt can be reacted with a reducing agent, e.g. sulfur and carbon monoxide, at a temperature of 150°-400° C., as in a process described in Dutch Patent application No. 7,209,028 published Dec. 27, 1972, which is relied upon and incorporated by reference herein. Alternatively, the ammonium salt can be reacted with carbon at a temperature of 370° to 390° C. as in Dutch Patent application No. 282,684 published Sept. 27, 1966 which is incorporated by reference herein or with the combustion products of an oil or gas burner at a temperature of 400° to 600° C., as in British Patent Specification No. 1,014,945 which is incorporated by reference herein The heat of the gas mixture, resulting from the thermal decomposition step, can be used to preheat and/or concentrate the sulfuric acid, at least some of which is in the form of an ammonium salt, prior to the thermal decomposition step. The result of the thermal decomposition step is the production of a gaseous mixture of ammonia and sulfur dioxide. This gaseous mixture is used to treat the remaining sulfuric acid, at least a part of which is in the form of an ammonium salt, which remainder was not treated in the thermal decomposition step. The step of contacting said sulfuric acid with said gaseous mixture can be effected, for instance, by passing the gas mixture of ammonia and sulfur dioxide into a column through which the liquid (sulfuric acid at least in part in the form of an ammonium salt thereof) is passed in countercurrent to said gas mixture, whereby the heat of neutralization is dissipated. Various other methods can be used to effect contact between the gas mixture and said sulfuric acid.

The result of contacting said sulfuric acid with said gas mixture is reaction between said ammonia of said gas mixture and sulfuric acid to produce ammonium sulfate, ammonium hydrogen sulfate or both. The sulfur dioxide escapes as sulfur dioxide and can be converted into sulfuric acid or oleum by conventional methods, and then said sulfuric acid or oleum can be employed to synthesize the ε-caprolactam.

Theoretically, and when no loss of raw materials occurs and when the composition of the sulfuric acid (at least a part of which is in the ammonium salt form) corresponds to ammonium hydrogen sulfate, then the amount of sulfuric acid (at least part of which is in the form of ammonium salt) in the reaction mixture is optimally divided in half and subjected to treatment in accordance with the invention. If should be noted that as conditions approach the optimal, the ε-caprolactam can be separated by extraction easily without the use of sulfuric acid and ammonia. Practically, however, losses of raw materials of this process always occur; for instance, losses of ammonia in the thermal decomposition will occur, and ammonia will have to be replenished. Thus, in practice it may be impossible to divide the sulfuric acid from the reaction mixture, which is partly neutralized with ammonia, in two equal parts which are subjected to the process of the invention.

The invention will be illustrated by the Description of Drawing below and the Example:

DESCRIPTION OF THE DRAWING

In the Drawing, A represents a reactor for conversion of cyclohexanone oxime into ε-caprolactam; B, a neutralizer for partial neutralization of the lactam/sulfuric acid mixture; C, an extraction device for extraction of the lactam from the lactam/ammonium hydrogen sulfate mixture formed in the partial neutralization; D, a neutralizer for complete or partial neutralization of the ammonium hydrogen sulfate; E, an installation for reductive decomposition of the ammonium hydrogen sulfate; and F, a sulfuric acid/oleum plant. Through line 1 cyclohexanone oxime is passed into the rearrangement reactor A, for instance a mixing-reactor provided with a stirrer or a vessel with a mixing-cyclone, to which sulfuric acid or oleum from the sulfuric acid/oleum plant F is supplied via line 2. Via line 3 the mixture flows to the neutralizer B, which is supplied with a solution of ammonium sulfate and ammonium hydrogen sulfate, originating from the ammonium hydrogen sulfate neutralizer D, via line 4; with ammonia via line 5; and with water via line 14. The amount of ammonia, supplied as ammonium sulfate, ammonium hydrogen sulfate and ammonia provides at least an equivalent amount of ammonium to react with one equivalent or sulfuric acid. Of course, it is possible fully or partly to replace the ammonia and the water by ammonia water. The rearrangement mixture neutralized to ammonium hydrogen sulfate flows via line 6 to the extraction device C, to which is passed, via line 7, a solvent for caprolactam, in which sulfuric acid, ammonium sulfate and ammonium hydrogen sulfate are poorly soluble, for instance benzene, toluene, 1,2-dichloroethane, chloroform, 1.1.2.2.-tetrachloroethane, ethyl ether or dibutyl carbinol. Caprolactam, dissolved in the extraction agent, is discharged from the system via line 13 and passed to an installation for recovery of the lactam (not exemplified in the drawing). The aqueous solution of ammonium hydrogen sulfate is discharged via line 9. Part of the ammonium hydrogen sulfate solution discharged via line 8 is conveyed to the decomposition device E via line 10 and decompossed under reductive conditions into a gas mixture principally containing ammonia, sulfur dioxide and water vapor. Via line 11 this gas mixture is led to the neutralizer D, which is supplied via line 9 with the remainder of the aqueous ammonium hydrogen sulfate solution originating from the extraction device C and supplied via line 8. With the aid of the ammonia present in the gas mixture from line 11, ammonium hydrogen sulfate is converted into ammonium sulfate in the neutralizer D. A gas mixture mainly containing sulfur dioxide escapes from the neutralizer D and is led to the sulfuric acid/oleum plate F via line 12. By concentrating, by evaporation, the solution passed to the decomposition device E via line 10, the water content can be maintained at the required level. From neutralizer D, the ammonium sulfate/ammonium hydrogen sulfate solution is conveyed -, after purification, purification being optional, - to neutralizer B via line 4.

Best Mode

Working according to the diagram of the Drawing, about 100 tons of ε-caprolactam are produced per day. The neutralization of the lactam/sulfuric acid mixture is carried out at atmospheric pressure, at a temperature of 40° C. In general, this neutralization can be carried out under the conditions disclosed in U.S. Patent Specification No. 3,336,298 which is hereby incorporated by reference. The ε-caprolactam formed is extracted with chloroform. The ammonium hydrogen sulfate formed in the neutralization is thermally decomposed in the presence of natural gas - in the way described in the British Patent Specification No. 1,014,945 - according to the gross equation:

$$NH_4HSO_4 + CH_4 + 1\tfrac{1}{2} O_2 \rightarrow NH_3 + SO_2 + 3 H_2O + CO_2$$

The composition of the various streams of materials, expressed in Kmole/hour, is set forth in the following table.

In this embodiment, the nitrogen is recovered from the ammonium sulfate/ammonium hydrogen sulfate solution in amounts up to 70%, in the form of ammonia, and the sulfur, in the form of sulfur dioxide in amounts up to 100%.

| line | oxime | oleum* | $NH_3$ | $NH_4HSO_4$/$(NH_4)_2SO_4$ | $CHCl_3$ | $SO_2$ | lactam |
|---|---|---|---|---|---|---|---|
| 1 | 37.6 | | | | | | |
| 2 | | 56 | | | | | |
| 3 | | 56 | | | | | 37 |
| 4 | | | | 56 | | | |
| 5 | | | 17 | | | | |
| 6 | | | | 112 | | | 37 |
| 7 | | | | | 230 | | |
| 8 | | | | 112 | | | |
| 9 | | | | 56 | | | |
| 10 | | | | 56 | | | |
| 11 | | | 39 | | | 56 | |
| 12 | | | | | | 56 | |
| 13 | | | | | 230 | | 37 |

*calculated as $H_2SO_4$

What is claimed is:

1. In a process for the recovery of ε-caprolactam from a reaction mixture containing ε-caprolactam and sulfuric acid in which process said sulfuric acid is partially neutralized to form an ammonium salt thereof and said lactam is separated from said partially neutralized sulfuric acid by extraction, the improvement comprising the steps of:
   a. contacting said reaction mixture with an ammonia source so as to only partially neutralize said sulfuric acid to an ammonium salt thereof,
   b. extracting and separating said lactam from said partially neutralized sulfuric acid,
   c. dividing said partially neutralized sulfuric acid from step (b) into first and second portions,
   d. decomposing said first portion into a gaseous mixture containing ammonia and sulfur dioxide,
   e. contacting said second portion with said gaseous mixture resulting in a further neutralized sulfuric acid and gaseous sulfur dioxide, and
   f. utilizing said further neutralized sulfuric acid as at least a portion of said ammonia source in step (a), wherein said partially neturalized sulfuric acid and said further neutralized sulfuric acid contain an ammonium salt selected from the group consisting of ammonium hydrogen sulfate, ammonium sulfate, or mixtures thereof.

* * * * *